United States Patent [19]

Alonso

[11] Patent Number: 4,935,030
[45] Date of Patent: Jun. 19, 1990

[54] MECHANICAL HEART VALVE PROSTHESIS

[75] Inventor: Manuel T. Alonso, Newport Beach, Calif.

[73] Assignee: Medtronic, Inc., Minneapolis, Minn.

[21] Appl. No.: 408,356

[22] Filed: Sep. 18, 1989

Related U.S. Application Data

[63] Continuation of Ser. No. 745,622, Jun. 17, 1985, abandoned.

[51] Int. Cl.⁵ .............................................. A61F 2/24
[52] U.S. Cl. ...................................................... 623/2
[58] Field of Search ............................................ 623/2

[56] References Cited

U.S. PATENT DOCUMENTS

| | | | |
|---|---|---|---|
| 4,078,268 | 3/1978 | Possis | 623/2 |
| 4,123,805 | 11/1978 | Kramer et al. | 623/2 |
| 4,276,658 | 7/1981 | Hanson et al. | 623/2 |
| 4,451,937 | 6/1984 | Klawitter | 632/2 |
| 4,535,483 | 8/1985 | Klawitter et al. | 623/2 |
| 4,605,408 | 8/1986 | Carpentier | 623/2 |

Primary Examiner—Alan W. Cannon
Attorney, Agent, or Firm—Reed A. Duthler; Joseph F. Breimayer

[57] ABSTRACT

A mechanical heart valve prosthesis has an annular base which defines a passageway for blood flow, and a pair of valve leaflets hingedly mounted within the annular base for regulating direction of the blood flow. The hinge mechanism includes camming indentations or hinge cavities located substantially in the corners of the valve leaflets at least on one side of each leaflet, and a plurality of camming or hinge pins which protrude radially inwardly from the annular base to engage both sides of the leaflets. Each of the hinge cavities is engaged by one hinge pin. During operation, the valve leaflets undergo certain wobbling or walking motion relative to the hinge pins whereby the hinged surfaces are continuously wiped to minimize the possibility for formation of incipient blood clots.

7 Claims, 1 Drawing Sheet

MECHANICAL HEART VALVE PROSTHESIS

This is a continuation of copending application Ser. No. 06/745,622 filed on 6/17/85 now abandoned.

BACKGROUND OF THE INVENTION

1. Field of the Invention

The present invention is in the field of heart valve prostheses. More particularly, the present invention is directed to an improved hinge mechanism for mechanical heart valve prostheses of the type having two valve leaflets which move in a limited pivoting motion to regulate the blood flow through the valve prostheses.

2. Brief Description of the Prior Art

Heart valve prostheses are well known in the art. Generally speaking, heart valve prostheses can be classified in two major types or categories. More particularly, one type of prostheses employs a tissue valve of animal (usually porcine) origin in its blood flow regulating valve mechanism. The other type of heart valve prosthesis utilizes a ball, a disc, valve leaflets or other mechanical valving devices to regulate the direction of blood flow through the prosthesis. The latter type of prosthesis is usually known in the art as "mechanical" heart valve prosthesis. For specific examples and detailed descriptions of the heart valve prostheses of the prior art, reference is made to U.S. Pat. Nos. 3,744,062; 3,835,475; 3,997,923; 4,364,126 and 4,106,129.

By their very nature, the mechanical heart valve prostheses have metal or plastic surfaces which, when exposed to the blood flow, are usually thrombogenic long after implantation of the prosthesis through open heart surgery. One of the problems the prior art heart valve prostheses have strived, but not fully succeeded to solve, relates to minimizing the thrombogenic effects created by the exposed metal or plastic surfaces.

Other problems which, generally speaking, all heart valve prostheses of the prior art have strived, but not fully succeeded to solve, relate to the ease of implantability, and reliability of operation of the valves. In this regard it will be readily appreciated by those skilled in the art that structural failure of an implanted artificial heart valve is likely to be fatal for the bearer of the heart valve. With regard to the ease of implantability of the artificial heart valves, it will be readily appreciated that open heart surgery presents difficult conditions. In order to minimize risk to the patient, the heart valve prostheses must be capable of being assembled and mounted in place in as few and simple steps as possible.

U.S. Pat. No. 4,276,658 discloses a "mechanical type" heart valve prosthesis which is designed to reduce the problem of thrombogenecity caused primarily by exposed metal or plastic surfaces of the valve. More specifically, it is known in this regard that thrombogenecity is caused not only by exposed metal or plastic surfaces, but also by areas or cavities disposed in an artificial heart valve which permit stagnation of blood flow and therefore permit the formation of incipient blood clots. Such areas of stagnated blood flow, or surfaces which are not continuously cleansed or wiped, are, therefore, undesirable and dangerous in the mechanical heart valve prostheses.

The artificial heart valve of U.S. Pat. No. 4,276,658 attempts to minimize the foregoing problem by providing surfaces coated with pyrolytic carbon, which is known to virtually lack thrombogenecity. Moreover, the mechanical heart valve of the above-noted patent employs two valve leaflets, each of which has an arcuate protrusion retained in matching depressions located in ears formed integrally with the annular base of the valve. An advantage of the mechanical heart valve of this patent is said to lie in the continuous "cleansing" or "wiping" action exerted by the moving arcuate portions, which help to remove any incipient blood clots from the depressions formed in the ears. However, the depressions, which must be kept free of blood clots, are relatively remotely disposed from the main stream of blood flow.

In light of the foregoing there is a need in the prior art for further improvements in mechanical heart valve prostheses with regard to simplicity and cost of construction, reliability of operation, and reduction of thrombogenecity. The mechanical heart valve of the present invention provides such an improvements.

SUMMARY OF THE INVENTION

It is an object of the present invention to provide a mechanical heart valve prosthesis which has no, or only minimal, thrombogenic surfaces exposed to the blood flow.

It is another object of the present invention to provide a mechanical heart valve prosthesis wherein the hinge mechanism is disposed in a location proximate to the mainstream of the blood flow so as to minimize the probability of incipient clot formation.

It is still another object of the present invention to provide a mechanical heart valve prosthesis wherein the surfaces of the moving valve leaflets effectively cleanse or wipe the hinge mechanism so as to minimize the probability of incipient blood clot formation in the hinge mechanism.

It is yet another object of the present invention to provide a mechanical heart valve prosthesis which is sufficiently rigid so as to minimize the risk of inadvertent dislodgement or seizure of the valve leaflets relative to their operating positions.

It is still a further object of the present invention to provide a mechanical heart valve prosthesis which meets the above-noted objectives and which is relatively simple and inexpensive to manufacture.

The foregoing objects and advantages are attained by a mechanical heart valve prosthesis having an annular base defining a blood passageway and a pair of valve leaflets which are mounted through a hinge mechanism for closing and opening the passageway for the blood flow. The hinge mechanism includes camming indentations disposed substantially in the corners of each of the valve leaflets at least on one side of each leaflet, and a plurality of camming pins protruding radially inwardly from the annular base to engage both sides of the leaflets. Each of the camming indentations is engaged by one camming pin. The two pins of each pair of the camming pins disposed to engage alternative sides of the leaflets are offset relative to one another in relation to the pivot line of the valve leaflets. The valve prosthesis of the invention is preferably made entirely of pyrolytic carbon. In the preferred embodiment, a metal ring, larger than the annular base, is concentrically mounted on the exterior of the annular base to provide additional rigidity to the base.

During operation of the mechanical valve prosthesis, the valve leaflets undergo limited "walking" or wobbling motion relative to the hinge pins whereby the surfaces of the indentations are continuously wiped or cleansed to prevent formation of incipient blood clots.

The features of the present invention can be best understood, together with further objects and advantages by reference to the following description taken together with the appended drawings.

DESCRIPTION OF THE PREFERRED EMBODIMENT

The following specification taken in conjunction with the drawings sets forth the preferred embodiment of the present invention. The embodiment of the invention disclosed herein is the best mode contemplated by the inventor for carrying out his invention, although it should be understood that several modifications can be accomplished within the scope of the present invention.

Figure 1:
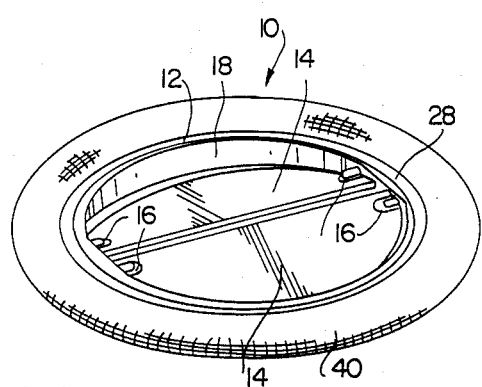
FIG. 1 is a perspective view showing the preferred embodiment of the mechanical heart valve prosthesis of the present invention.
Figure 2:
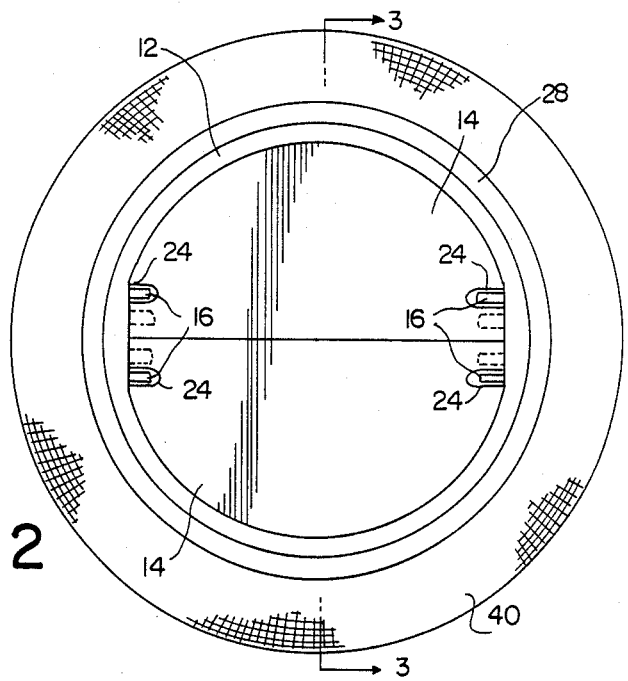
FIG. 2 is a top view showing the preferred embodiment of the mechanical heart valve prosthesis of the present invention.
Figure 3:
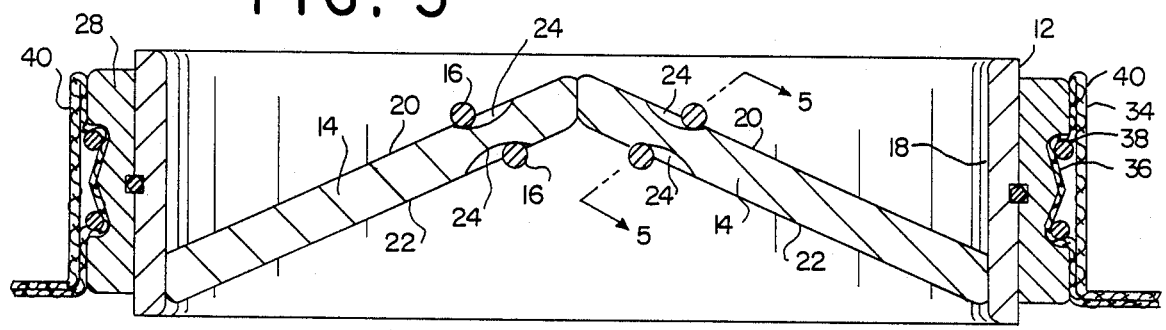
FIG. 3 is a cross-sectional view of the preferred embodiment, the view being taken on lines 3,3 of FIG. 2.

Referring now to the drawing Figures, and particularly to FIGS. 1 through 3, the preferred embodiment 10 of the mechanical heart valve prosthesis of the present invention is disclosed.

The heart valve prosthesis 10 includes an annular base 12 which defines a passageway for flow of blood (not shown) through the valve prosthesis 10. As is usual in the heart valve prosthesis art, the annular base 12 has varying dimensions to accomodate patients of varying ages and body sizes. The dimensions of the annular base 12 also depends on whether the prosthesis is used in-plantations replacing mitral, aortal or tricuspid heart valves.

Two valve leaflets 14 are mounted in the interior of the annular base 12 to open and close the passageway for flow of blood. Each of the valve leaflets 14 is substantially semicircular in configuration, as is best shown on FIGS. 1 and 2. Whereas valve leaflets of heart valve prostheses, per se, are old in the art, (and are described for example in U.S. Pat. No. 4,276,658, the specification of which is expressly incorporated herein by reference) the manner of hingedly mounting the valve leaflets 14 in the herein described heart valve prosthesis 10 is new, and comprises the principal novel feature of the present invention.

Thus, a plurality of camming hinge pins 16 protrude radially inwardly from the interior surface 18 of the annular base 12 and engage the upper and lower surfaces of the valve leaflets 14. The camming hinge pins 16, in conjunction with the indentations 24 in the upper and lower surfaces of the valve leaflets 14, together comprise means for retaining the leaflets 14 in the annular base 12 and for permitting movement of the leaflets while regulating flow of blood in the blood passageway. The upper and lower surfaces of the valve leaflets 14 bear the reference numerals 20 and 22, respectively. In this regard it is noted that the valve leaflets 14, even when closed, preferably occupy an angular position in the annular base 12, as is shown on FIG. 3, although this feature, per se, is also known in the art, and is described in the above-referenced U.S. Pat. No. 4,276,658. Of course, when the valve leaflets 14 are open to permit flow of blood through the valve prosthesis 10, they occupy a more extreme angular position relative to the annular base 12, as is shown on FIG. 4.

The radially inwardly protruding camming pins 16 are short in relation to the blood passageway, that is, relative to the internal diameter of the annular base 12. Therefore, the camming hinge pins 16 cause only minimal, insignificant interference with the blood flow. By way of example, in an actual embodiment of a heart valve prosthesis fabricated in accordance with the present invention, the internal diameter of the annular base 12 is approximately 0.825" long and the camming hinge pins 16 are approximately 0.030" long. The hinge pins 16 preferably are cylindrical, as is best shown on FIGS. 3 and 4. The hinge pins 16 are also preferably integrally fabricated with the annular base 12.

The hinge pins 16 are arranged in the interior surface 18 of the annular base 12 in pairs to provide two hinge or pivot points for each valve leaflet 14. More particularly, as is shown on the drawing Figures, each pair of the hinge pins 16 engages one corner of the valve leaflets 14 on the upper and lower surfaces, 20 and 22, of the respective valve leaflet 14. Through this arrangement a pivot line is defined for each valve leaflet 14. The hinge pins 16 of each pair are offset relative to one another in relation to the pivot line, so that the hinge pins 16 engaging the upper surfaces 20 are more remote from the pivot line than the hinge pins 16 engaging the lower surfaces 22.

Figure 5:
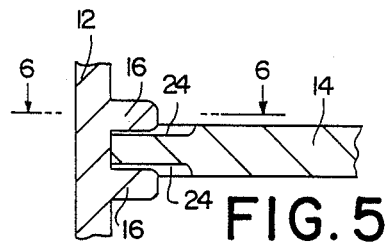
FIG. 5 is a partial cross-sectional view taken on lines 5,5 of FIG. 3.

Pins 16 protrude inwardly from the interior surface of annular base 12, each indentation 24 on base 12 being operatively engaged by one pin 16. As can be seen in FIG. 5, the surfaces of pins 16 which engage recesses 24 in upper and lower surfaces 20 and 22 are spaced closer together to one another than those portions of the upper and lower surfaces 20 and 22 adjacent to said recesses 24.

It will be readily recognized by those skilled in the art in light of the present disclosure that various configurations for the hinge pins 16 are possible within the scope of the present invention, the criteria being that the hinge pins 16 provide appropriate camming surfaces to cooperate with the hereinafter described hinge cavities 21.

Thus, a plurality of indentations or hinge cavities 24 are provided substantially in the corners 26 of the valve leaflets 14 to operatively engage the hinge pins 16. In the herein shown preferred embodiment, the indentations or hinge cavities 14 are present on both the upper and lower surfaces, 20 and 22 respectively, of the valve leaflets 14. Each of the indentations or hinge cavities has a concave curved, preferably cylindrical, interior surface and is dimensioned to cooperate with the hinge pins 16 to permit limited pivoting movement of the valve leaflets 14 within the annular base 12. In this regard it is noted that the dimensions of the hinge cavities or indentations 24 are small in relation to the dimensions of the annular base 12, or the valve leaflets 14. Substantially correct dimensions of the indentations 24 relative to the rest of the valve prosthesis 10 are shown for example on FIG. 2. In the above-noted actual exemplary embodiment of the heart valve prosthesis of the invention, the concave cylindrical surface of the hinge cavities 24 is formed with a radius of approximately 0.85", whereas the diameter of the cylindrical hinge pins 16 is approximately 0.030".

In alternative embodiments of the valve prostheses of the present invention which are not specifically shown herein, the indentations or hinge cavities 24 are present only on the upper surfaces 20 of the valve leaflets 14. Thus, in these alternative embodiments (not shown), one hinge pin of each pair of hinge pins engages a concave arcuate hinge cavity on the top surface of the respective valve leaflet, whereas the other hinge pin of the same pair engages the substantially flat lower surface of the respective valve leaflet. The just described structure (not shown) offers certain advantages from the standpoint of reduced expense of fabricating the valve prostheses of the present invention.

Returning now to the description of the preferred embodiment 10 illustrated in the drawing Figures, operation of the valve prosthesis is described as follows. The valve leaflets 14 open and close, that is, move up and down relative to the annular base 12 while being held by the hinge pins 16. FIG. 3 shows the valve leaflets 14 in fully closed position, whereas the partial view of FIG. 4 shows one valve leaflet 14 in a substantially open position.

Figure 4:
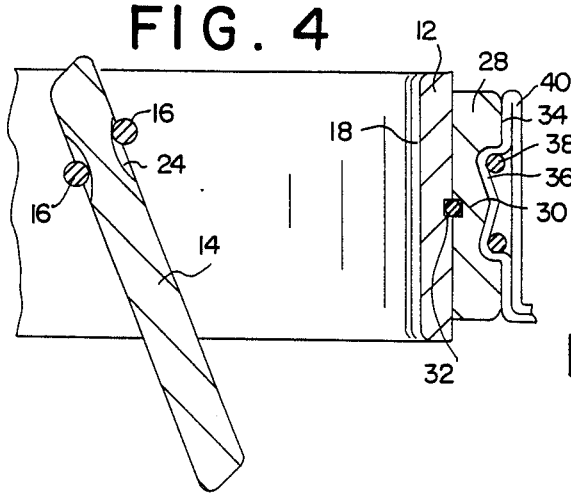
FIG. 4 is a partial view analogous to the cross-sectional view of FIG. 3, but showing the valve leaflet of the preferred embodiment in an open position.
Figure 6:
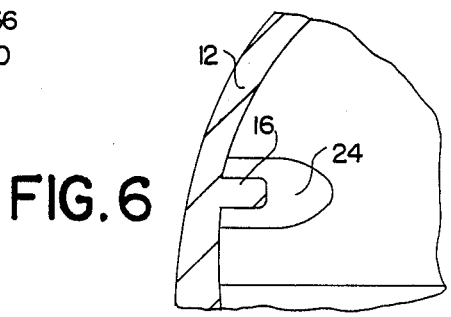
FIG. 6 is a partial view taken on lines 6,6 of FIG. 5.

A very advantageous and important consequence of the above-described structure, which becomes apparent from an inspection of FIGS. 3 and 4, is that the valve leaflets 14 wobble or "walk" relative to the hinge pins 16 while they move up and down to open and close the heart valve prosthesis 10 for blood flow. Consequently, there is a continuous cleansing or wiping action of the hinge pins 16 and of the hinge indentations 24. This wiping action eliminates, or very substantially reduces the possibility for formation of incipient blood clots in the prosthesis. Another important advantage of the above-described structure is that the hinge pins 16 and the corresponding indentations 24 are disposed substantially in the mainstream of the blood flow, thereby still further reducing the possibility for formation of incipient blood clots. This is in sharp contrast with the prosthesis described in U.S. Pat. No. 4,276,658, where the hinge mechanism includes a cavity of depression relatively hidden from the blood flow.

The annular base 12 and the valve leaflets 14 of the mechanical heart valve prosthesis 10 of the present invention are preferably made entirely of pyrolytic carbon in accordance with processes which are known in the art. As is known, pyrolytic carbon material has very little thrombogenecity, and is generally considered safe for use in mechanical heart valve prostheses.

Although various ways known in the art may be utilized to add further rigidity to the annular base 12, and to mount the heart valve prosthesis into the surrounding living tissue (not shown), FIGS. 1 through 3 illustrate the preferred manner of accomplishing the foregoing objectives. Thus, the annular base 12 is friction fitted in a metal ring 28 and is secured to the metal ring 28 by a wire 30 disposed in circumferential grooves 32 of the ring 28 and the annular base 12. The metal ring 28 and the wire 30 both comprise such metals, e.g. titanium or cobalt-chrome, which are considered acceptable for surgical implantation into the human body. The metal ring 28 can be biolized or coated with pyrolytic carbon. Because the assembled annular base 12 and metal ring 28 are rigid, the probability of dislocating one or more of the valve leaflets 14 from the implanted heart valve prosthesis 10, or causing their seizure through an accidental shock or jolt, is virtually eliminated.

The exterior surface 34 of the metal ring 28 incorporates a second groove 36 configured to accept threads 38 and a substantially conventional sewing ring 40. As is well known in the art, the sewing ring 40 is affixed by sutures (not shown) to the living tissue (not shown) when the heart valve prosthesis 10 is implanted.

What has been described above is an improved mechanical heart valve prosthesis which is relatively simple to construct and which minimizes the possibility for stagnation of blood flow and formation of incipient blood clots. Several modifications of the mechanical heart valve prosthesis of the present invention may becomes readily apparent to those skilled in the art in light of the foregoing disclosure. Therefore, the scope of the present invention should be interpreted solely from the following claims, as such claims are read in light of the disclosure.

What is claimed is:

1. A heart valve prosthesis comprising:
   an annular base which defines a blood passageway, said annular base having an interior surface;
   valve means fitted in said annular base for regulating the flow of blood through said passageway defined by said annular base, said valve means comprising two leaflets, each of said leaflets having a first arcuate edge which is configured to interface with the interior surface of said annular base in a fluid flow sealing relationship therewith and a second edge which is configured to interface with the other of said leaflets in a fluid flow sealing relationship therewith, each of said leaflets further having upper and lower surfaces, at least one of said upper and lower surfaces of each of said leaflets defining two indentations, each indentation limited to the area substantially adjacent to both said first and second edges of said leaflet; and
   four pairs of protrusions extending from said annular base inwardly towards the blood passageway defined through said annular base, the indentations defined in said at least one of said upper and lower surfaces of said leaflets and said protrusions jointly comprising means for retaining said leaflets in said annular base and for permitting movement of said leaflets while regulating flow of blood through said blood passageway defined by said annular base, said means for retaining said leaflets consisting of said four pairs of protrusions and the indentations defined in said at least one of said upper and lower surfaces of said leaflets, each of said protrusions engaging either the upper or lower surface of one of said leaflets, at least one of said protrusions in each of said four pairs of protrusions engaging with one of said indentations defined in said at least one of said upper and lower surfaces of each of said leaflets, the portions of said protrusions engaging said upper and lower surfaces of said leaflets being spaced closer together than said upper and lower surfaces of said leaflets in the areas of said leaflet adjacent to the indentations defined in said one of said upper and lower surfaces of each of said leaflets.

2. The heart valve prosthesis of claim 1 wherein the upper and lower surfaces of each one of said leaflets each define a pair of indentations, each located in and limited to the area adjacent both said first and second edges of each of said leaflets.

3. The heart valve prosthesis of claim 1 or claim 2 wherein said protrusions are substantially cylindrical.

4. The heart valve prosthesis of claim 1 or claim 2 wherein said annular base and said leaflets comprise pyrolytic carbon.

5. The heart valve prosthesis of claim 1 or claim 2 wherein said protrusions and the indentations defined in said at least one of said upper and lower surfaces of each of said leaflets jointly comprise means for permitting limited wobbling motion of said leaflets relative to said protrusions.

6. The heart valve prosthesis of claim 1 or claim 2 wherein in their closed position, said valve leaflets are disposed at an angle relative to said annular base.

7. The heart valve prosthesis of claim 1 or claim 2 wherein the leaflets are mounted within said annular base such that movement of each of said leaflets defines a pivot axis, and wherein those of said protrusions which engage said upper surfaces of each of said leaflets are offset relative to said pivot axes from those of said protrusions which engage said lower surfaces of said leaflets.

* * * * *